United States Patent [19]
Ichikawa et al.

[11] 4,303,070
[45] Dec. 1, 1981

[54] SYRINGE

[75] Inventors: Toshiji Ichikawa; Teruko Watanabe, both of Tokyo, Japan

[73] Assignee: Terumo Corporation, Tokyo, Japan

[21] Appl. No.: 189,148

[22] Filed: Sep. 22, 1980

[30] Foreign Application Priority Data

Oct. 9, 1979 [JP] Japan .................................. 54-130178

[51] Int. Cl.³ .............................................. A61M 5/00
[52] U.S. Cl. ................................. 128/218 P; 128/234
[58] Field of Search ............... 128/218 P, 218 R, 234, 128/215, 224; 92/245, 249

[56] References Cited

U.S. PATENT DOCUMENTS

| | | | |
|---|---|---|---|
| 3,147,753 | 9/1964 | Nogier et al. ................... | 128/218 P |
| 3,151,617 | 10/1964 | Baum ............................. | 128/218 P |
| 3,166,993 | 1/1965 | Blenkle .......................... | 128/218 P |
| 3,176,595 | 4/1965 | Schwartz ........................ | 128/218 P |
| 4,074,715 | 2/1978 | Geiger ........................... | 128/218 P |

Primary Examiner—John D. Vasko
Attorney, Agent, or Firm—Bacon & Thomas

[57] ABSTRACT

A syringe includes an outer cylinder, a gasket having at least one part which slidably contacts the inner wall of the cylinder and being made of an elastomer material including a block copolymer having styrene units at both terminal ends, and means for sliding the gasket inside the cylinder. The slidably contacting part is compressed inside the cylinder at a compressiblity C (%) of a predetermined range selected according to a particular inner diameter of the cylinder. The product of the total contact area S (mm²) at the compressibility C (%) of the contacting part with the inner wall of the cylinder with the compressibility C (%) is about 350 to about 900.

21 Claims, 3 Drawing Figures

SYRINGE

The present invention relates to a syringe and more particularly to a syringe which includes a gasket with improved slidability.

A syringe generally comprises an outer cylinder, a gasket encased therein for sliding movements, and a plunger for sliding the gasket. Important characteristics required for this type of syringe are air-impermeability, water-impermeability and slidability of the gasket. Air- and water-impermeability is required for eliminating leakage of the liquid and introduction of the air between the outer face of the gasket and the inner wall of the outer cylinder when charging or discharging such a liquid inside the syringe. The slidability is important for facilitating the charging and discharging of the liquid inside the syringe. In addition to these requirements, a medical syringe, in particular, must not adversely affect any medicine or blood with which it comes in contact.

The gasket of a conventional syringe is made of a rubber material such as natural rubber, isoprene rubber or styrene-butadiene rubber which is vulcanized with sulfur. This gasket is encased inside an outer cylinder of plastic material. Although this type of conventional gasket has good air- and water-impermeability, it does not have good slidability inside the outer cylinder even if silicone is applied to both the entire outer face of the gasket and the inner wall of the outer cylinder. The use of this gasket has thus been relatively inconvenient. Furthermore, a conventional gasket requires a comparatively great force to start its movement from the stopped position inside the outer cylinder (i.e., the initial movement is hard to effect). Thus, if an attempt is made to move the gasket from the stopped position to a relatively nearby target position, the force required to effect this movement sometimes results in a movement which overshoots the target position (i.e., knocking is thus noted). Due to this, it is difficult to correctly charge or discharge a desired amount of a liquid sample.

In addition, in a conventional gasket of the type described above, additives such as sulfur, a vulcanization-accelerator, and a filler are added to the rubber material during the manufacture. Thus, when the gasket comes in contact with blood or medicines such as injection solutions in use, these additives may be eluted into the blood or medicines. Thus, the gasket has presented problems for medical use. Furthermore, since the conventional gasket is manufactured by molding which requires the vulcanization step for converting a plastic material into an elastic material, the productivity has thus been inferior.

It is one of the objects of the present invention to provide a syringe with a gasket which is superior in air- and water-impermeability as well as in slidability.

It is another object of the present invention to provide a syringe which does not adversely affect liquids charged into it.

It is still another object of the present invention to provide a syringe which may be manufactured in a simple manner.

To the above and other ends, the present invention provides a syringe comprising an outer cylinder; a gasket having at least one part which slidably contacts the inner wall of said outer cylinder under the compressed condition forming air-and water-tight seal and being made of a colorable thermoplastic elastomer material including a block copolymer having a mean molecular weight between about 50,000 and about 200,000 and having the general formula

(where St represents styrene units, A represents a unit derived from an unsaturated hydrocarbon having 2-5 carbon atoms or combinations thereof, and m, m' and n represent the mol % of each unit, the sum of m and m' being 2-20 mol %); and means for sliding said gasket inside said outer cylinder, said slidably contacting part being compressed inside said outer cylinder at a compressibility C (%) of a predetermined range selected accoring to a particular inner diameter of said outer cylinder, the product of the total contact area S (mm$^2$) of said slidably contacting part with the inner wall of said outer cylinder with said compressibility C (%) being about 350 to about 900, the value of S(mm$^2$) being measured at said compressibility C (%).

The relation between the air-and water-impermeability and the slidability is such that when one is good the other is necessarily bad. Irrespective of this fact, the gasket must satisfy both characteristics. The present inventors have noted that the compressibility (to be defined hereinafter) of the gasket inside the outer cylinder and the total area of contact between the gasket and the inner wall of the outer cylinder under the compressed condition greatly influence the air-and water-impermeability and the slidability. As a result of research, taking into consideration the influence of the liquid on the gasket and the ease of manufacture of such gasket, the present inventors have found that a gasket which has improved air-and water-impermeability and slidability in comparison with conventional gaskets can be obtained by using as a gasket material an elastomer material including a block copolymer of the above-mentioned general formula and, if desired, a certain amount of a polyolefin-based resin mixed therewith and by satisfying the relation between the above-mentioned compressibility and the total contact area to be described hereinafter. The present invention has thus been established.

This invention can be more fully understood from the following detailed description when taken in conjunction with the accompanying drawings, in which.

A syringe in accordance with one embodiment of the present invention will now be described with reference to the accompanying drawings. In the drawings, the same reference numerals denote similar parts or portions.

Figure 1:
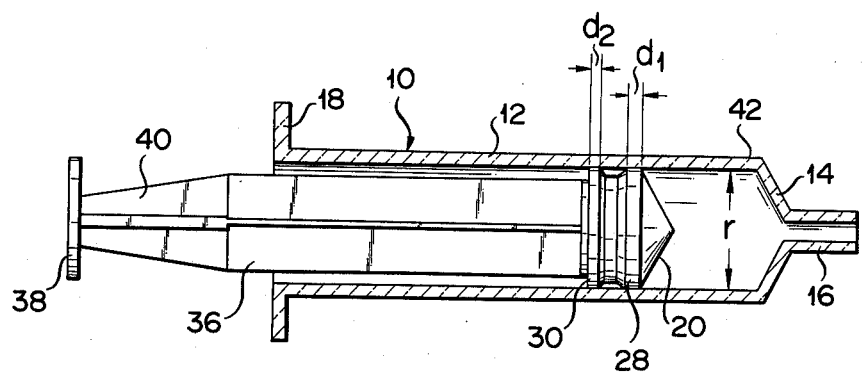
FIG. 1 is a partial sectional side view of a syringe in accordance with the present invention.

Referring to FIG. 1, a syringe 10 has an outer cylinder 12 which in turn has at its front end a tapered portion 14 connected to a nozzle 16 for connection with a canula. An elliptical flange 18 to be used as a finger stopper for pressing the plunger with the fingers is formed at the rear end of the outer cylinder 12. Although the outer cylinder 12 may be made of any suitable hard material, it is preferably made of a transparent material. Especially when the syringe is intended to be a disposable syringe, it is preferably made of a transparent plastic material such as polypropylene.

The outer cylinder 12 encases a gasket 20 which can be slid inside the outer cylinder 12 by means of a plunger 36.

As a result of research on the material and shape of the gasket, the present inventors first found that a gasket which is good in moldability, has excellent slidability and air-and water-impermeability, and is suitable for mass-production can be obtained by using a thermoplastic elastomer material including a block copolymer of the following formula:

$$(St)_{\overline{m}}(A)_{\overline{n}}(St)_{m'} \qquad (1)$$

In the above formula (1), A represents a unit derived from an unsaturated hydrocarbon having 2–5 carbon atoms or combinations thereof. Examples of such unsaturated hydrocarbons are ethylene, propylene, butylene, isobutylene, butadiene and isoprene. Isoprene and a combination of ethylene with isobutylene is especially preferred.

The mean molecular weight of the block copolymer as represented by the formula (1) is about 50,000 to about 200,000, and preferably about 500,000 to about 150,000. When the mean molecular weight is below about 50,000 or above about 200,000, the injection moldability is degraded.

As has already been described, in the formula (1), m, m' and n represent the mol % of each unit and satisfy the condition $[(m+M')/(m+m'+n)] \times 100 = 2$ to 20 mol %. The sum of styrene units (St) at both terminal ends of molecules shares 2–20 mol % of the block copolymer (thus, the total molecular weight of the styrene units is about 1,000 to about 40,000). When the percentage of the styrene (m+m') is below 2 mol %, the repellency becomes inferior; when it exceeds 20 mol %, the material becomes too hard and is inconvenient to use. The total mol % of the styrene units is preferably 2–10%.

The block copolymer of the formula (1) may be manufactured by any conventional method. An alkyl lithium such as butyllithium and styrene are added to an inert solvent such as an alkane and the mixture is kept at room temperature to 65° C. so as to obtain a styrene polymer terminating at one end in a lithium group. By adding one or more monomers constituting the block A in the formula (1) to this reaction system, a living block copolymer of the formula $(St)_{\overline{m}}A$—Li is obtained. When styrene is added to this mixture, a block copolymer of the formula (1) is obtained. When butadiene or a combination of butadiene with other monomers, etc., is used for obtaining the block A, it is preferable that the unsaturated bonds present in the block A be hydrogenated. Such hydrogenation may be performed, for example, by the method disclosed in the Japanese Patent Publication No. 48-3555. According to this method, the block copolymer is hydrogenated in the presence of a reacting mixture of a cobalt or nickel compound with an alkyl aluminum at a temperature of below 125° C. and at a pressure of below 70 kg/cm². Thereafter, a predetermined amount of Lewis base or alcohol is added, and the final hydrogenation is performed.

Sometimes, the block copolymer of the formula (1) still does not satisfy the properties required for the gasket material. In order to compensate for this, it is preferred that a polyolefin-based resin be added. The polyolefin-based resin is added in an amount of 5–200 parts by weight, and preferably 10–180 parts by weight based on 100 parts by weight of the block copolymer of the formula (1). The polyolefin-based resin to be used includes polyethylene, polypropylene, an ethylenepropylene copolymer and chlorinated polyethylene. Further, liquid paraffin can be added in order to provide softness. It is further possible to add an antioxidant such as dibutyl hydroxytoluene. The elastomer thus obtained is white to colorless and can be colored with various colorants such as carbon black and red iron oxide. Due to this, gaskets may be discriminated by coloring gaskets of different diameters with different colors. Further, since this elastomer material is elastic and thermoplastic at ordinary temperature, it may be melted and formed, preferably by injection molding, into a desired gasket for a cylinder in a molding cycle of about 7–20 seconds.

The gasket to be used in the syringe of the present invention will now be described from the perspective of its shape.

A conventional gasket of vulcanized rubber is not satisfactory in slidability, especially in its intial movability as has already been pointed out. In this type of conventional gasket, the part which slidably contacts the inner wall of the outer cylinder forms a relatively sharp peak and is comparatively easy to deform. Relating to this problem, the present inventors were convinced that an extra force required for deformation of the peak is partially attributable to the defective slidability of the conventional gasket. After various studies, the present inventors found that the slidability is improved by flattening the top surface of the slidably contacting part of the gasket. Based on this, the present inventors further studied the relation of the compressibility of the gasket and the area of contact between the gasket and the inner wall of the outer cylinder. As a result of this, it was confirmed that a gasket which is improved in slidability and air-and water-impermeability may be obtained by satisfying the conditions that the slidably contacting part be compressed at a compressibility C (%) of a predetermined range selected according to the particular inner diameter of an outer cylinder, and the product (S×C) of the total contact area S (mm²) of the slidably contacting part of the gasket and inner wall of the outer cylinder with said compressibility C (%) be about 350 to about 900, the value of S (mm²) being measured at this compressibility.

Figure 2:
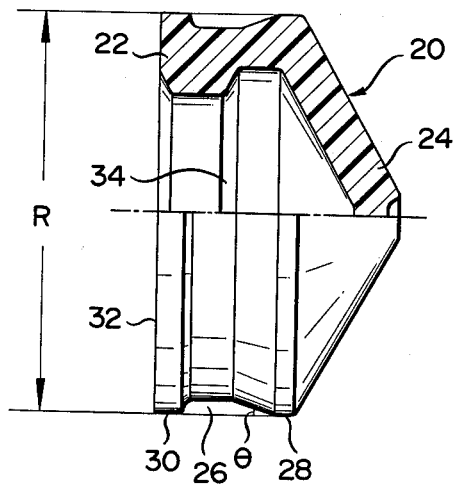
FIG. 2 is a partial sectional side view of a gasket used in the syringe in accordance with the present invention.

The gasket thus obtained has a cylindrical body 22 as shown in FIG. 2. A conical head part 24 is formed integrally with one end face of this body 22, this one end face being the bottom of this conical head part. This conical head part fits with the tapered portion 14 of the outer cylinder 12. An annular groove 26 is formed on the circumferential face of the body 22, thus forming two ribs 28 and 30 having flat top faces defined by the circumferential face of the body 22. These annular ribs 28 and 30 constitute slidably contacting part of gasket which contacts the inner wall of the outer cylinder 12 under the compressed condition. A hole 34 extends from the other end face 32 of the body 22 toward the inside of the body 22. Inside this hole 34 is inserted and fixed the plunger 36 having a cross-shaped cross section (FIG. 1). A disk part 38 to be pressed by fingers is formed at the rear end of the plunger 36. The plunger 36 is reduced in width starting at a position about ⅓ of its axial length from its rear end toward the disk part 38 to form a width reduced part 40. This part 40 has a matted surface and is made thicker for easier handling.

In the present invention, the compressibility C (%) is defined in relation to the free outer diameter of the slidably contacting parts 28 and 30 of the gasket 20 (the outer diameter R in the non-compressed condition) and the inner diameter r of the outer cylinder 12 as follows:

$$C (\%) = \frac{R - r}{R} \times 100$$

The total contact area S (mm$^2$) may be obtained by the widths $d_1$ (mm) and $d_2$ (mm) of the slidably contacting parts 28 and 30, respectively, inside the outer cylinder 12, and by the inner diameter r of the outer cylinder as follows:

$$S(mm^2) = 2\pi r(d_1 + d_2)$$

The product of S and C is intended to represent the product of the absolute values of each factor, and is about 350—about 900. When this product is below 350, the air-impermeability is degraded; when it exceeds 900, slidability is degraded.

It is to be noted here that the compressibility C (%) varies in each case according to the inner diameter of the particular outer cylinder used and that the product of the compressibility C (%) as determined according to the inner diameter of this outer cylinder with the corresponding total contact area S (mm$^2$) must be about 350—about 900.

The relation between the inner diameter of the outer cylinder and the compressibility C (%) is shown in Table 1 below:

TABLE 1

| Syringe capacity | Inner diameter of outer cylinder, average (mm) | Compressibility C (%) General range | Compressibility C (%) Preferable range |
|---|---|---|---|
| 1 cc | 4.7 | 3.9–18.3 | 6.0–15.3 |
|  | 6.5 | 2.8–11.6 | 6.8–9.1 |
| 2.5 cc | 9.0 | 2.0–9.5 | 3.3–7.7 |
| 5 cc | 13.0 | 0.6–6.8 | 1.9–5.5 |
| 10 cc | 15.8 | 1.1–5.7 | 2.0–4.5 |
| 20 cc | 20.15 | 1.0–4.7 | 1.7–3.8 |
| 30 cc | 23.1 | 1.5–6.3 | 2.1–5.5 |
| 50 cc | 29.1 | 2.5–6.3 | 3.0–5.7 |

Referring back to FIG. 2, it was found that the slidability of the gasket depends particularly on the deformability of the slidably contacting part 28 at the front end. Thus, in order to make it more difficult for the slidably contacting part 28 to deform, the annular groove 26 is so shaped that it is gradually tapered away from the top face of the slidably contacting part 28. This improves the slidability. The tapering angle θ is generally 10–30 degrees, and preferably 15–25 degrees. With this tapering, the slidably contacting part 28 will thus have a trapezoidal sectional area having its bottom side on the extension line of the bottom side of the groove 26.

For using the syringe of the present invention for medical purposes, the syringe is sterilized with the gasket encased inside the outer cylinder using ethylene oxide gas at a temperature of about 60—about 65° C. for about 6—about 8 hours. After the sterilization, the compressibility changes by the permanent setting of the elastomer material of the present invention. However, it suffices to be within the range indicated in Table 1. In other words, even if the compressibility of the gasket before sterilization is not within the range shown in Table 1 in consideration of the expected permanent setting, it suffices to be within the range shown in Table 1 after sterilization. Sterilization can also be effected by γ ray irradiation.

Figure 3:
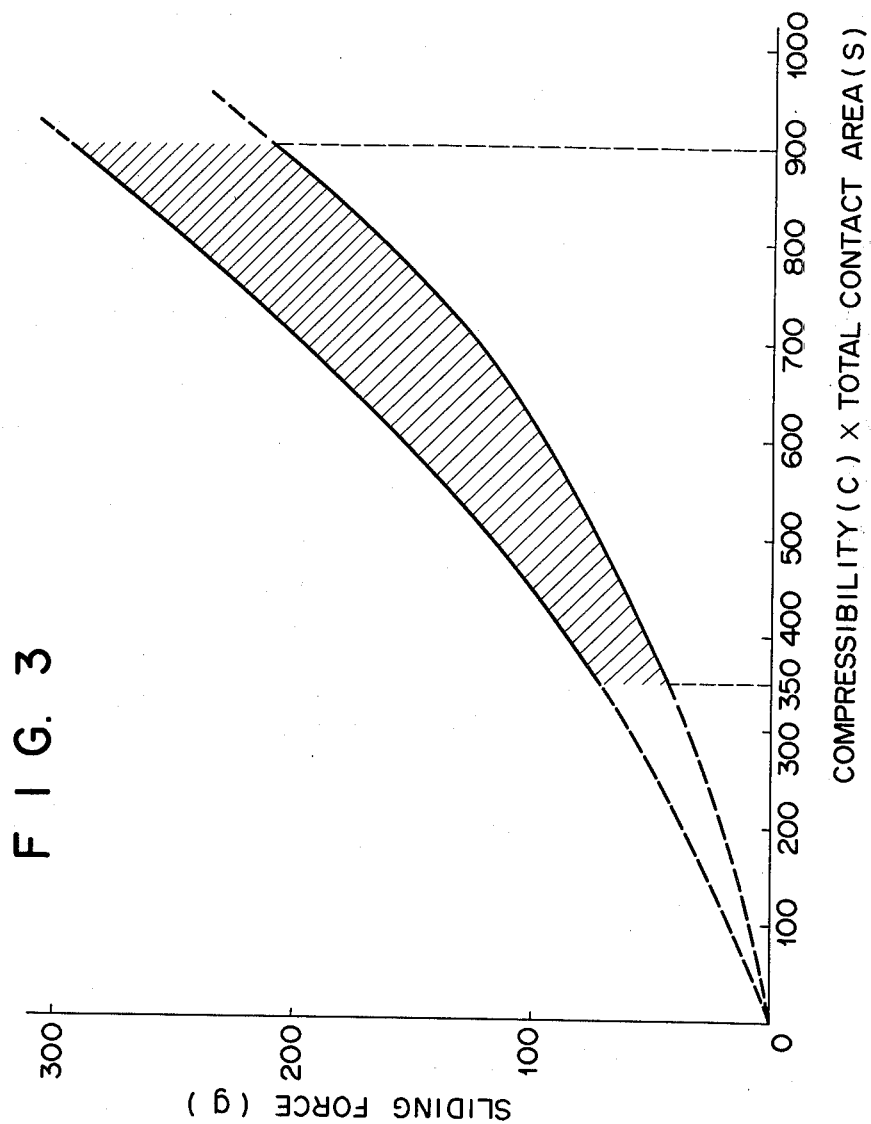
FIG. 3 is a graph showing a characteristic of the syringe in accordance with the present invention.

Many syringes according to the present invention, including the comparative examples, were manufactured and the relation of the product of the compressibility C (%) and the total contact area S (mm$^2$) to the sliding force were measured. The results are shown in FIG. 3. The water-impermeability of each syringe was also measured by the following method. With each syringe, the slidably contacting part 28 of the gasket was set at a position 2 mm away from a shoulder 42 of the outer cylinder 12, at substantially the central position of the outer cylinder 12, and at the maximum calibrated value of the outer cylinder 12. About 1–2 cc of water was charged into the space between the outer cylinder 12 and the gasket 20. Air was blown through the nozzle 16 at a pressure of 2.5 kg/cm$^2$ in the case of syringes of 50, 30 or 20 cc in capacity; 3.0 kg/cm$^2$ for syringes of 10 cc in capacity; 3.5 kg/cm$^2$ for syringes of 5 cc in capacity; 4.0 kg/cm$^2$ for syringes of 2.5 cc in capacity; and 5.0 kg/cm$^2$ for syringes of 1 cc in capacity. Observations were made to determine whether water entered the sapce between the slidably contacting parts 28 and 30. As a result, water entered when S×C was below 350 and water did not enter when S×C was 350 or more. It is seen from these results that improved air-impermeability and slidability may be obtained when the product of the compressibility C (%) and the total contact area S (mm$^2$) is about 350—about 900.

The present invention will now be described below by way of examples.

EXAMPLE

Ten syringes of the present invention of the shape shown in FIGS. 1 and 2 were manufactured for each capacity as shown in Table 2. The initial moving force and the sliding force were measured. For comparison, the initial moving force and the sliding force for conventional syringes were also measured. The results are shown in Table 2. In Table 2, both the initial moving force and the sliding force are represented by their mean values. The outer cylinder was made of polypropylene and the gasket in accordance with the present invention was made by injection molding an elastomer material A containing 150 parts by weight of ethylene-propylene copolymer based on on 100 parts by weight of the block copolymer of formula (1) and an elastomer material B containing 20 parts by weight of ethylene-propylene copolymer based on 100 parts by weight of the block copolymer of formula (1) under a cylinder temperature of 200°–210° C., an injection time of 5 seconds and a cooling time of 10 seconds.

TABLE 2

| | Syringe capacity | | | | | |
|---|---|---|---|---|---|---|
| | 5 cc | | 10 cc | | 20 cc | |
| Item | Prior Art | Present Invention | Prior Art | Present Invention | Prior Art | Present Invention |
| Inner diameter of outer cylinder (mm) | 13.0 | 13.0 | 14.8 | 15.8 | 20.15 | 20.15 |

TABLE 2-continued

| | Syringe capacity | | | | | |
|---|---|---|---|---|---|---|
| | 5 cc | | 10 cc | | 20 cc | |
| Item | Prior Art | Present Invention | Prior Art | Present Invention | Prior Art | Present Invention |
| Compressibility C (%) | 3.7 | 4.4 | 3.3 | 3.7 | 1.2 | 3.1 |
| Contact width ($d_1 + d_2$) (mm) | 1.10 | 2.40 | 1.50 | 2.80 | 2.15 | 3.65 |
| Total contact are S (mm$^2$) | 44.92 | 104.05 | 69.27 | 138.98 | 136.10 | 231.10 |
| C × S | 166.20 | 457.82 | 228.59 | 514.23 | 163.32 | 716.41 |
| Initial moving force (g) | 682 | 148 | 880 | 242 | 550 | 304 |
| Sliding force (g) | 220 | 67 | 220 | 110 | 286 | 198 |

The results of the elution analysis conducted according to the Liquid-transportation rubber stopper test method of the ninth amended version of the Japanese Pharmacopeia are shown in Table 3 along with the results obtained with the conventional gaskets. The gaskets of the present invention showed negative results in the hemolysis test and the cellular poisoning test.

TABLE 3

| | Present Invention | | | |
|---|---|---|---|---|
| Item | A* | B* | Prior Art | Standards |
| ΔpH | 0.15 | 0.13 | 1.29 | below 1.0 |
| ΔConsumption of permanganic acid | 0.25 | 0.75 | 7.65 | below 2.0 |
| Bubbling | within 1 min. | within 1 min. | within 3 min. | within 3 min. |
| Absorption of ultraviolet rays | 220 nm 0.02 | 220 nm 0.04 | 230 nm 0.59 310 nm 2.59 | below 0.2 |
| Heavy metal Zn | ND* | ND* | 0.725 ppm | below 0.5 ppm |
| Pb | ND* | ND* | ND* | below 1.0 ppm |
| Cd | ND* | ND* | | |

Note:
A is the elastomer material A.
B is the elastomer material B.
ND is below the detection limit.

From the above results, it is seen that the slidability of the gaskets of the present invention is far superior to conventional gaskets, independently of the fact whether the comparisons were made for the syringes of the same capacities or for the syringes of different capacities. The gasket of the syringe of the present invention generates a far smaller amount of elution and is safer for medical purposes than the gasket of a conventional syringe.

In summary, since the gasket is improved in air-impermeability and slidability in a syringe of the present invention, the handling of it is easy. Moreover, with the syringe of the present invention, since the initial movability of the gasket is good, the knocking, which is common in conventional gaskets, is not seen. Accordingly, it is possible to correctly charge and discharge a predetermined amount of a liquid sample with the syringe of the present invention.

Since the gasket used in the syringe of the present invention is made of a thermoplastic elastomer material which does not contain sulfur, sulfur is not eluted into the chemicals or blood with which the gasket comes in contact. Sulfurous acid gas is not generated by burning the gasket after use. Since the gasket do not contain heavy metals such as zinc, elution of such metals is not seen. There is no free sulfur or metal to react with the chemical solution.

Further, since the gasket for the syringe of the present invention may be injection molded, the dimension stability is excellent. The gasket of the present invention is made of a thermoplastic elastomer which has excellent flow characteristics in comparison with vulcanized rubber used in conventional gaskets, and the distortion of the molded body is therefore small.

Further, since the gasket of the present invention is made of a thermoplastic elastomer which is injection moldable, the properties of the material are the same before and after molding unlike the material of the conventional gasket which is plastic before the molding and elastic after the molding. Accordingly, it is possible to obtain a gasket of desired properties by appropriately selecting materials of desired properties.

As has already been described, since the gasket of the present invention shows a negative reaction to hemolysis, it may be safely used for medical injections and for drawing blood. Further, the thermoplastic elastomer which is the material for the gasket is heat-resistant so that it can easily withstand γ ray irradiation and the temperatures of sterilization with ethylene oxide, transportation, and storage.

Since the gasket of the present invention can be injection molded, the manufacturing time can be vastly shortened in comparison with conventional manufacture which includes the vulcanization step. With the gasket of the present invention, mold-releasability is good, facilitating mass-production. The step for removing the flashes may also be eliminated, resulting in economical manufacture. Further, the runner and sprue of the thermoplastic elastomer after molding this gasket may be reused to injection mold another gasket with the same properties. Thus, the raw material may be used with efficiency and economy.

Furthermore, since the gasket of the present invention has excellent slidability, it does not require a coating of silicone oil. In order to obtain still better slidability, it suffices to add a suitable amount of silicone oil to the thermoplastic elastomer for injection molding and a coating step is not required.

What is claimed is:

1. A syringe comprising an outer cylinder; a gasket having at least one part which slidably contacts the inner wall of said outer cylinder under the compressed condition forming a water-tight seal and being made of a colorable thermoplastic elastomer material including a block copolymer having a mean molecular weight between about 50,000 and about 200,000 and having the general formula $$(St)_m(A)_n(St)_{m'}$$

(where St represents styrene units, A represents a unit derived from an unsaturated hydrocarbon having 2-5 carbon stoms or combinations thereof, and m, m' and n represent the mol % of each unit, the sum of m and m' being 2-20 mol %); and means for sliding said gasket inside said outer cylinder, said slidably contacting part being compressed inside said outer cylinder at a compressibility C (%) of a predetermined range selected according to a particular inner diameter of said outer cylinder, the product (S×C) of the total contact area S (mm²) of said slidably contacting part with the inner wall of said outer cylinder with said compressibility C (%) being about 350 to about 900, the value of S (mm²) being measured at said compressibility C (%).

2. A syringe as claimed in claim 1 wherein said elastoner material contains 5 to 200 parts by weight of polyolefin-based resin based on 100 parts by weight of the block copolymer.

3. A syringe as claimed in claim 2 wherein said gasket comprises a cylindrical body defined by a first end face, a second end face and a circumferential face; a conical head portion integrally formed with said first end face of said body; and an annular groove formed in said circumferential face of said body, said annular groove forming two slidably contacting parts having flat top faces each defined by part of said circumferentail face.

4. A syringe as claimed in claim 3 wherein said slidably contacting parts have trapezoidal sectional areas.

5. A syringe as claimed in claim 4 wherein the top face of the contacting part and the side of the groove intersects at an angle of 10° to 30°.

6. A syringe as claimed in claim 2 wherein A represents a unit derived from a combination of ethylene and isobuthylene, or isoprene.

7. A syringe as claimed in claim 2 wherein said block copolymer has a mean molecular weight between about 50,000 and about 150,000.

8. A syringe as claimed in claim 2 wherein said bock copolymer contains a total of 2 to 10 mol % of the styrene units.

9. A syringe as claimed in claim 2 wherein said polyolefin-based resin is polyethlene, polypropylene or ethylene-propylene copolymer.

10. A syringe as claimed in claim 2 wherein said elastoner material contains the polyolefin-based resin in an amount of 10 to 180 parts by weight based on 100 parts by weight of the block copolymer.

11. A syringe as claimed in any one of claims 1 to 10 wherein said compressibility C (%) is selected from the range of 0.6 to 18.3 % according to the particular inner diameter of the outer cylinder.

12. A syringe as claimed in claim 10, wherein said outer cylinder has an inner diameter of about 4.7 mm, and the compressibility C (%) is selected from the range of 3.9 to 18.3 %.

13. A syringe as claimed in claim 10, wherein said outer cylinder has an inner diameter of about 6.5 mm, and the compressibility C (%) is selected from the range of 2.8 to 11.6 %.

14. A syringe as claimed in claim 10, wherein said outer cylinder has an inner diameter of about 9.0 mm, and the compressibility C (%) is selected from the range of 2.0 to 9.5 %.

15. A syringe as claimed in claim 10, wherein said outer cylinder has an inner diameter of about 13.0 mm, and the compressibility C (%) is selected from the range of 0.6 to 6.8%.

16. A syringe as claimed in claim 10, wherein said outer cylinder has an inner diameter of about 15.8 mm, and the compressibility C (%) is selected from the range of 1.1 to 5.7 %.

17. A syringe as claimed in claim 10, wherein said outer cylinder has an inner diameter of about 20.1 mm, and the compressibility C (%) is selected from the range of 1.0 to 4.7%.

18. A syringe as claimed in claim 10, wherein said outer cylinder has an inner diameter of about 23.1 mm, and the compressibility C (%) is selected from the range of 1.5 to 6.3 %.

19. A syringe as claimed in claim 10, wherein said outer cylinder has an inner diameter of about 29.1 mm, and the compressibility C (%) is selected from the range of 2.5 to 6.3%.

20. A gasket for a syringe, made of a colorable elastomer material including a block copolymer having a mean molecular weight between about 50,000 and about 200,000 and having the general formula $$(St)_m(A)_n(St)_{m'}$$

where St represents styrene units, A represents a unit derived from an unsaturated hydrocarbon having 2-5 carbon atoms or combinations thereof, and m, m' and n represent the mol % of each unit, the sum of m and m' being 2-20 mol %.

21. A syringe as claimed in claim 1 wherein said elastomer material contains 5 to 200 parts by weight of polyolefin-based resin based on 100 parts by weight of the block copolymer.

* * * * *